(12) United States Patent
Sumii et al.

(10) Patent No.: US 6,457,862 B1
(45) Date of Patent: Oct. 1, 2002

(54) ANALYZER SYSTEM HAVING SAMPLE EXCHANGER

(75) Inventors: Koushi Sumii; Kiyotaka Kasai, both of Takatsuki (JP)

(73) Assignee: Rigaku Industrial Corporation, Takatsuki (JP)

( * ) Notice: Subject to any disclaimer, the term of this patent is extended or adjusted under 35 U.S.C. 154(b) by 41 days.

(21) Appl. No.: 09/611,531

(22) Filed: Jul. 6, 2000

(30) Foreign Application Priority Data

Jul. 12, 1999 (JP) ............................................ 11-196997

(51) Int. Cl.⁷ ................................................ H05G 1/00
(52) U.S. Cl. .......................................... 378/208; 378/79
(58) Field of Search .............................. 378/208, 69, 79, 378/68; 422/65, 104; 206/569, 438, 558

(56) References Cited

U.S. PATENT DOCUMENTS

| | | | | |
|---|---|---|---|---|
| 4,040,533 A | * | 8/1977 | De Boer et al. ............ 214/310 |
| 5,345,395 A | * | 9/1994 | Griner ......................... 364/497 |
| 5,363,885 A | * | 11/1994 | McConnell et al. ........... 141/1 |
| 6,111,930 A | * | 8/2000 | Schipper ...................... 378/79 |

* cited by examiner

Primary Examiner—Robert H. Kim
Assistant Examiner—Jurie Yun
(74) Attorney, Agent, or Firm—Antonelli, Terry, Stout & Kraus, LLP

(57) ABSTRACT

An analyzer system to ease sample handling having a sample exchanger with an analyzer apparatus, a sample table, and a transfer unit for taking the sample from the table into the analyzer apparatus. The sample table includes a base and a tray for holding the samples supported so they tray can be pulled out in front of the base. With this, it is possible for an operator to handle the samples easily, in particular samples located deep on the table usually difficult to handle. The operator may pull out the tray in the front direction from the base, without having to stand. The tray may be separately carried to a computer controller of the analyzer apparatus, thereby enabling input of sample data while mounting or installing the samples onto the tray to prevent erroneous inputting.

19 Claims, 6 Drawing Sheets

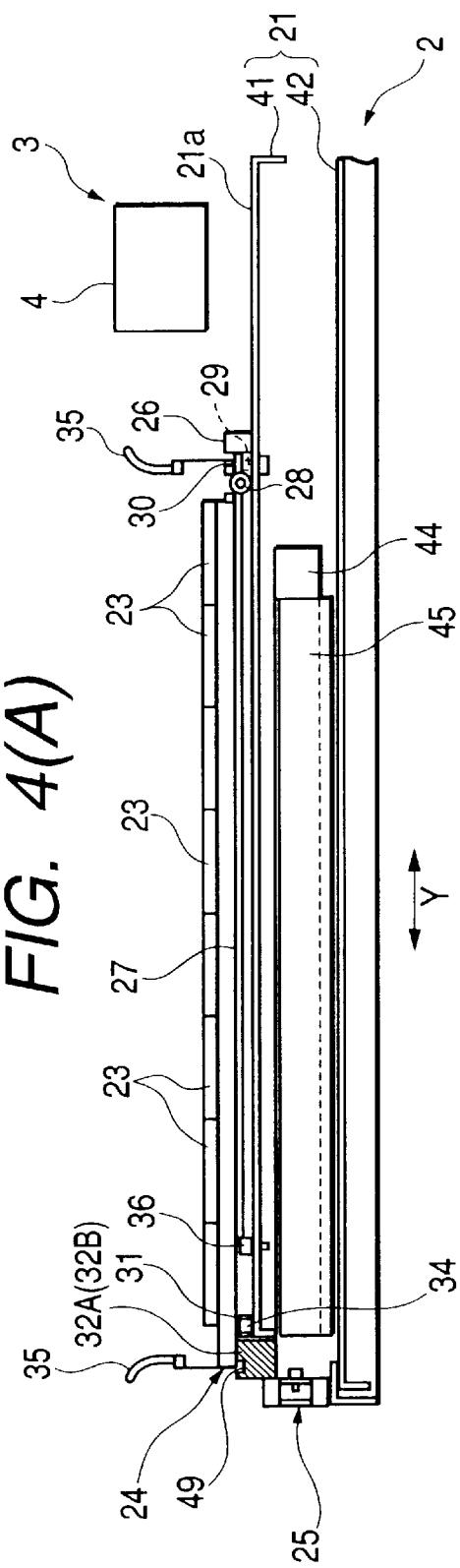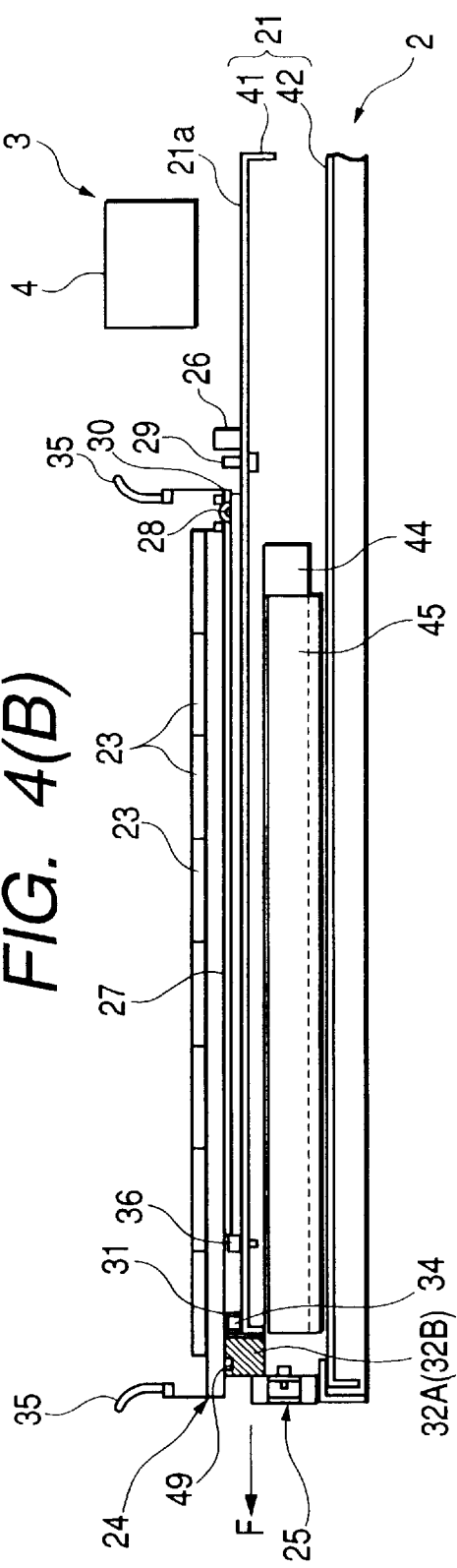

ANALYZER SYSTEM HAVING SAMPLE EXCHANGER

BACKGROUND OF THE INVENTION

1. Field of the Invention

The present invention relates to an analyzer system having a sample exchanger, being equipped with an analyzer apparatus, such as an X-rays spectroscopic analyzer, an emission spectrophotometer or an X-ray photoelectron spectrometer, a sample table on which a plurality of samples to be analyzed in this analyzer apparatus are held, and a transfer means for taking out the sample from the sample table to transfer it into the analyzer apparatus.

2. Description of Prior Art

In an X-rays analyzer system having such kind of the sample exchanger, conventionally, a plural number of samples which are aligned lengthwise and breadthwise on a sample table are automatically taken out by a transfer means so as to be transferred into an inlet opening of the X-rays spectroscopic analyzer, then after completing the analysis of the sample by the X-rays spectroscopic analyzer, the sample is turned or brought back to the original position on the sample table again, or to an arbitrary position which is assigned to, and this operation is repeated continuously. Control of such the operation is conducted by a personal computer, into which are inputted the positions of those samples on the sample table and an ID data relating to an order of the analysis thereof, and so on.

As such of the sample table, there was known one of a stable table type on which those samples are held at the respective positions, fixedly, however with this type of the table, it is not easy for an operator to treat or handle the samples, in particular to install and remove the samples in the deep or rear position on the table while sitting on a seat, therefore she/he must do it from a stand-up position. Also, when inputting into the computer of personal type the ID data relating to the samples held on the sample table, and for preventing from errors in the inputting, the personal computer must be located in the vicinity of the sample table so that various kinds of ID data, including such as the holding positions relating to those samples, are inputted every time when one of the samples is taken out from a separate storage and is held on the sample table, therefore the position for locating or providing the computer is limited.

SUMMARY OF THE INVENTION

According to the present invention, for taking such the problems mentioned above into the consideration, an object is to provide an analyzer system having a sample exchanger, with which the samples can be handled easily.

For achieving the object mentioned above, according to the present invention, there is provided an analyzer system equipped with a sample exchanger, comprising: an analyzer apparatus for analyzing a sample; a sample table for holding a plurality of said samples thereon; and a transfer means for taking out the sample from the sample table and into said analyzer apparatus, wherein said sample table comprises: a base; and a tray for holding the samples thereon, being supported so that it can be pulled out in a front of the base. Here, said sample includes both the sample itself and the sample which is held in a sample holder.

With this analyzer system, it is possible for an operator to handle easily, even the samples which are located in deep on the sample table so that there is difficulty to handle them, by pulling out the tray in front from the base, without necessity of standing up, for example, while sitting on a chair. Also, if a computer as the controller of the analyzer apparatus is located, being separated from the sample table, it is possible to separate the tray from the base so as to carry it in a front of the computer, thereby to input ID data relating to the samples on that tray into the computer, therefore the setting position of the computer should not be restricted within the vicinity of that sample table.

Also, according to the present invention, in the analyzer system as mentioned in the above, wherein the sample table further comprises a movement catcher means, being able to be pulled out in front together with the tray engaged with a lower surface thereof when the tray is pulled out, for supporting the tray on the base. With such the analyzer system, the tray is supported by the movement catcher means for supporting the tray thereon when the tray is pulled out from the base, therefore it is possible to support the tray with a good stability, even under the condition of being pulled out.

Further, according to the present invention, in the analyzer system as mentioned in the above, wherein the trays are provided in a plural number thereof, and for each of a smaller number of the trays is provided the movement catcher. With such the analyzer system, it is possible to use the movement catcher means for supporting the smaller number of trays, in common, as one unit, thereby bringing the system simple in the structure thereof. Also, when the trays are supported on the movement catcher means in a number being smaller than that assigned in advance, an excessive area occurs on the surface of the movement catcher means, therefore it is possible to exchange the sample(s) on the tray with ease, by using the excessive area for the purpose of provisional positioning of the sample(s) or for resting arms thereon, etc.

Further, according to the present invention, in the analyzer system as mentioned in the above, wherein a positioning member for positioning the tray is provided at a position corresponding to a front portion of the tray when laying within the storage position in the base, so that it abuts upon a projecting portion on a lower surface of a rear portion of the tray when it is pulled out, and wherein an engagement portion and a first engaged portion, for engaging with each other to hold the tray in the storage position, are provided on the front portion of the tray and the positioning member, respectively. With such the analyzer system, the positioning of the tray is carried out by abutting the projecting portion on the lower surface of the rear portion of the tray upon the positioning member of the base, therefore there is no chance that the tray comes off from the base when it is pulled out. Also, engaging the engagement portion at the front of the tray with the engaged portion of the positioning member of the base, it is possible to keep the tray laying in the storage position with a good stability.

Further, according to the present invention, in the analyzer system as mentioned in the above, wherein a positioning member for positioning the tray is provided at a position corresponding to the front portion of the tray when laying within the storage position in said base, so that it abuts upon a projecting portion on a lower surface of a rear portion of the tray when it is pulled out, wherein an engagement portion and a first engaged portion, for engaging with each other to hold the tray in the storage position, are provided on the front portion of the tray and the positioning member, respectively, and in a front portion of the movement catcher means is provided a second engaged portion being selectively engaged with the first engagement portion of the positioning member. With such the analyzer system, under the condition that the engagement portion of the tray is engaged with the second engaged portion at the front of the movement catcher means, the movement catcher means is pulled out as one body together with the tray when pulling out the tray from the base, therefore it is possible to pull out the tray as it is under the condition of being supported by the movement catcher means, thereby obtaining the pull-out of the tray with good stability.

Further, according to the present invention, in the analyzer system as mentioned in the above, wherein a positioning member for positioning the tray is provided at a position corresponding to the front portion of the tray when laying within the storage position in the base, so that it abuts upon a projecting portion on a lower surface of a rear portion of the tray when it is pulled out, and wherein the projecting portion on the lower surface of the rear portion of the tray includes a roller which runs on a tray mounting surface of the base. With this, the positioning of the tray is carried out by abutting the projecting portion on the lower surface of the rear portion of the tray upon the positioning member of the base, therefore there is no chance that the tray comes of f from the base when it is pulled out. Also, the projecting portion at the rear portion of the tray is constructed with the roller, therefore it is possible to carry out the pull-out of the tray smoothly, by holding or grasping the front portion of the tray so as to let it to run on the tray mounting surface of the base.

BRIEF DESCRIPTION OF THE DRAWINGS

FIG. 4(A) is a vertical cross-section view for showing a condition that a tray is stored within the same sample exchanger, and FIG. 4(B) a vertical cross-section view for showing another condition that the tray is engaged with a jig of movement catcher thereof;

DESCRIPTION OF PREFERRED EMBODIMENTS

Hereinafter, embodiments according to the present invention will be fully explained by referring to the attached drawings.

Figure 1:
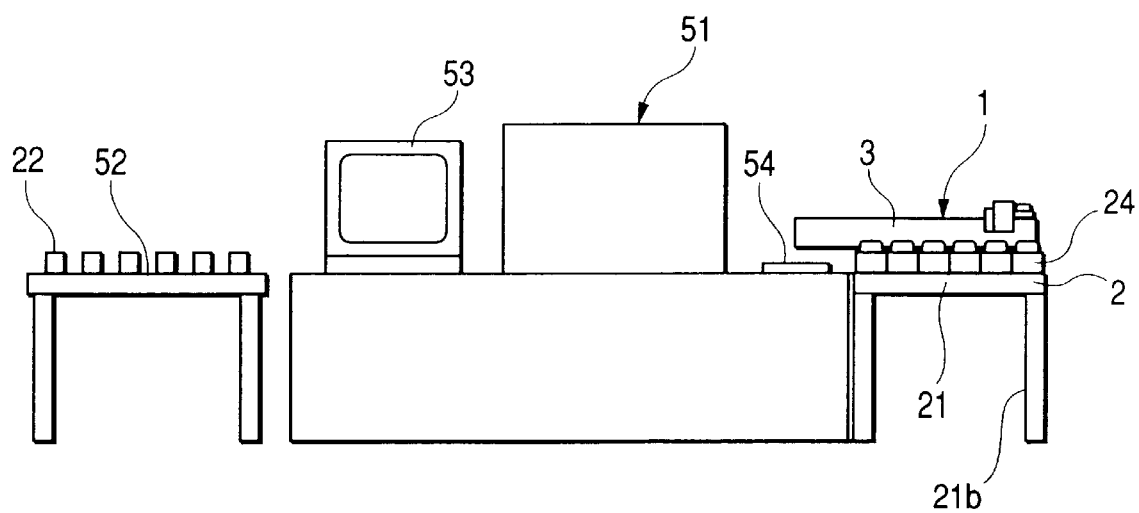
FIG. 1 is a side view for showing an entire X-rays analyzer system having the sample exchanger and the X-rays analyzer apparatus, according to the present invention.

FIG. 1 shows a front view of an entire X-rays analyzer system, having an X-rays analyzer apparatus 51, such as a fluorescence X-rays analyzer or a diffraction analyzer, a sample exchanger 1, according to an embodiment of the present invention, and a sample storage table 52. In the same figure, a computer 53 as a controller is provided or installed on an upper part of the X-rays analyzer apparatus 5 at the left-hand side thereof, while in the upper part at the right-hand side is formed a sample inlet opening 54 for putting the sample into and out from the X-rays analyzer apparatus 51. On the sample storage table 52, there are laying a large number of positioned sample holders 22, each holding a sample therein. The sample exchanger 1 is provided or positioned on a sample table 2. The sample holders 22 are moved from the sample storage table 52 on the sample table 2, and are carried from here into the sample inlet opening 54 by the exchanger 1, thereby being transferred into a predetermined position by a transfer apparatus positioned within the X-rays analyzer apparatus 51. At this predetermined position, the sample which is held in the sample holder 22 receives irradiation of X-rays, thereby to be analyzed therewith. The sample holder after completion of the analysis thereof is returned back onto the sample storage table 52, along with the route reverse to the mentioned above. However, the samples which are transferred in the manner mentioned above should not be restricted only to the case that it is transferred while being held in the sample holder 22, but also includes a case where the sample is transferred by itself as a single body.

Figure 2:
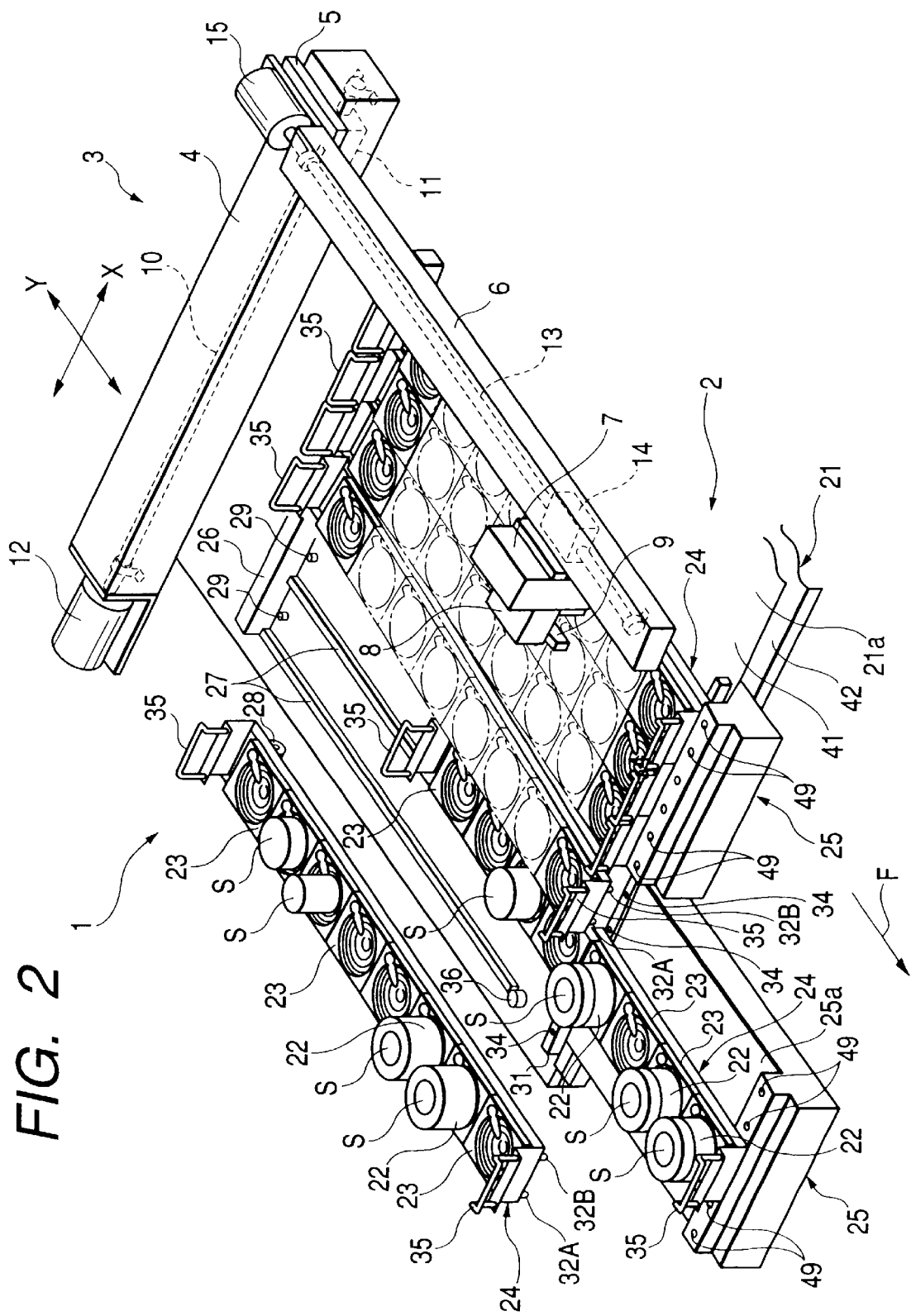
FIG. 2 is a perspective view for showing the sample exchanger of the X-rays analyzer apparatus, according to one embodiment of the present invention.
Figure 3:
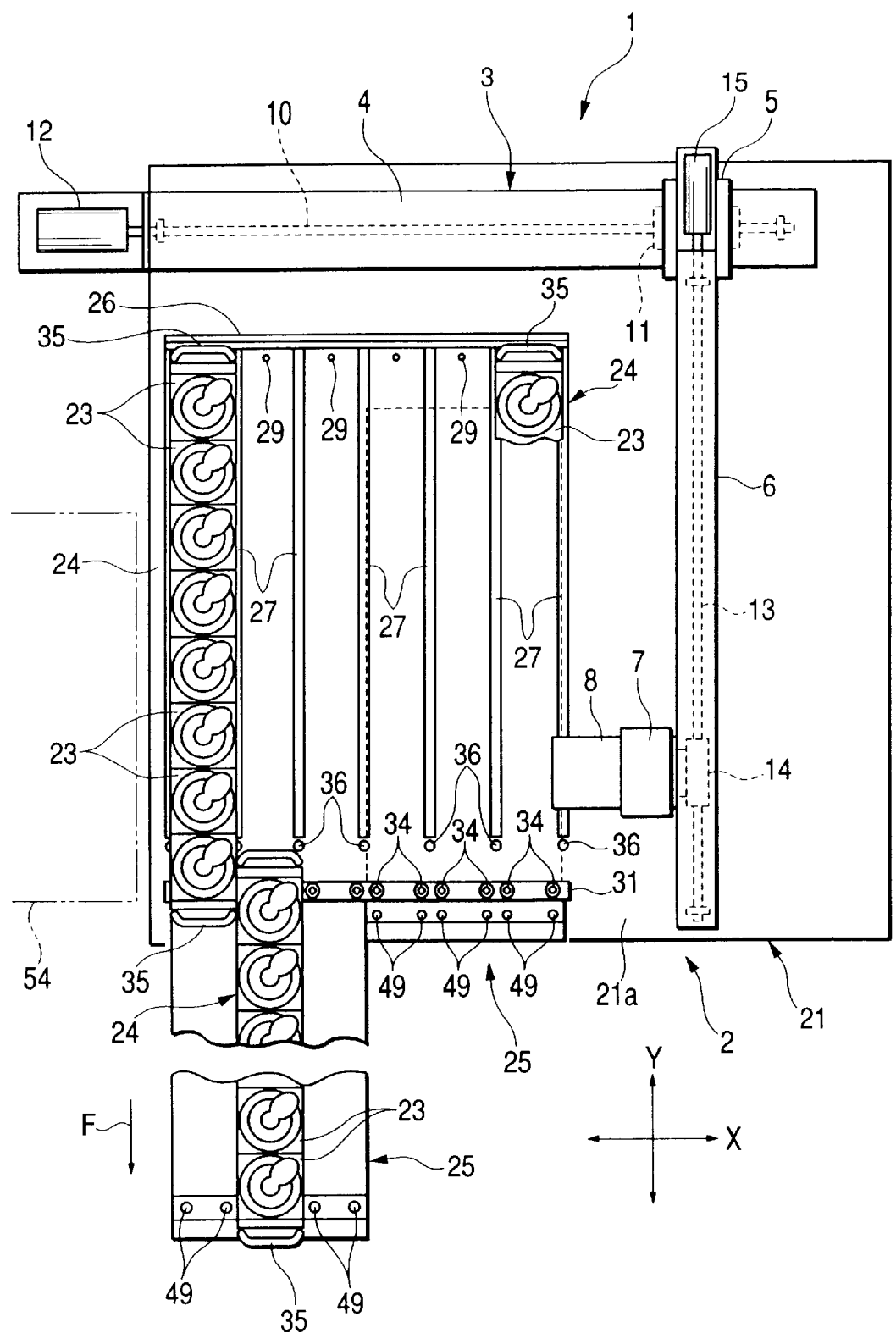
FIG. 3 is a front view of the same sample exchanger.

FIG. 2 shows a perspective view of the sample exchanger 1 mentioned above. This sample exchanger 1 comprises the sample table 2 on which the plurality of samples S to be analyzed by the X-rays analyzer are kept, and a transfer means 3 for taking out the sample S from the sample table 2 so as to transfer it into the sample inlet opening 54 (FIG. 3) of the X-rays analyzer.

The transfer means 3 comprises, in a deep or rear position on the table 2, a horizontal moving stage 5, being freely movable along with a horizontal rail 4 which is positioned directing into a horizontal position X of the sample table 2, a vertical moving stage 7, being fixed on the horizontal moving stage 5 and freely movable along with a vertical rail 6 which is positioned in a vertical direction Y (i.e., in a direction from front to behind) on the sample table 2, an elevating stage 8, being provided on the vertical moving stage 7 and freely movable up and down, and a chuck 9, being supported on the elevating stage 8 and for holding the sample S on the sample table 2 and/or at the sample inlet opening 54 (FIG. 3) in the X-rays analyzer, or for releasing the sample S from the holding condition thereby.

Within the above-mentioned horizontal rail 4, there is provided a ball screw 10 along with a longitudinal direction thereof, wherein to a ball nut 11 screwed with this ball screw 10 is connected the above-mentioned horizontal moving stage 5, thereby the horizontal moving stage 5 being movable in the horizontal direction X, by rotationally driving the ball screw 10 through a servo-motor 12 which is provided at an end portion of the horizontal rail 4.

Within the above-mentioned vertical rail 6, there is provided a ball screw 13 along with a longitudinal direction thereof, wherein to a ball nut 14 screwed with this ball screw 13 is connected the above-mentioned vertical moving stage 7, thereby the vertical moving stage 7 being movable in the vertical direction Y, by rotationally driving the ball screw 13 through a servo-motor 15 which is provided at an end portion of the vertical rail 6. The above-mentioned elevating stage 8 is driven upward and/or downward through an elevating mechanism which is provided in the vertical moving stage 7, though not shown in the figure.

The above-mentioned sample table 2 is supported on a flat tray mounting surface 21a on a base 21, being able to be pulled out into a forward direction F of the base 21, and it comprises trays 24, each holding a plurality of mounting bases 23 aligning on a line in a direction from front to behind, onto which are mounted the sample holders 22 each being the sample itself or holding the sample therein, and a plurality of jigs or plates 25 for catching the movement (or movement catcher) and for supporting the trays 24 on the base 21, which are engaged with the trays 24 on the bottom surfaces thereof and are able to be pulled out together with them when they are pulled out.

Each of the above-mentioned tray 24 is made from a member, being long in the pulling-out direction of the sample table 2, and the trays 24 are aligned in a plural number thereof, for example, six (6) are aligned here. At the front and behind of the tray 24 are provided handles 35, respectively, for carrying it with ease thereby. Also, the above-mentioned jigs 25 of movement catcher are provided by the number of two (2) thereof, and they are so arranged or positioned that one of the jigs 25 of movement catcher corresponds to three (3) of the trays which are adjacent in the horizontal direction. In this manner, the number of jigs 25 of movement catcher is smaller than that of the trays, thereby the apparatus becomes simple in the construction thereof.

In the deep or rear portion of the tray mounting surface 21a on the above-mentioned base 21, there is provided a positioning member 26, extending in the horizontal direction X, for receiving therein a rear edge of the tray 24 when laying in a storage position thereof. Also, on the tray mounting surface 21a of the base 21, there are provided guide rails 27 for guiding the pull-out and return-back to the storage positions of the trays 24, extending in the vertical direction Y, respectively, at the positions corresponding to both side portions of each of the trays 24 which are aligned directing in the horizontal direction. Further, at a front edge position of each of the guide rails 27 on the above-mentioned tray mounting surface 21a, there is provided a guide roller 36, respectively, for guiding the tray 24 so as to enter into between the corresponding guide rails 27 at the right-hand side and the left-hand side, smoothly, when the tray 24 is turned back to the original storage position from the pulled-out position thereof.

Figure 7:
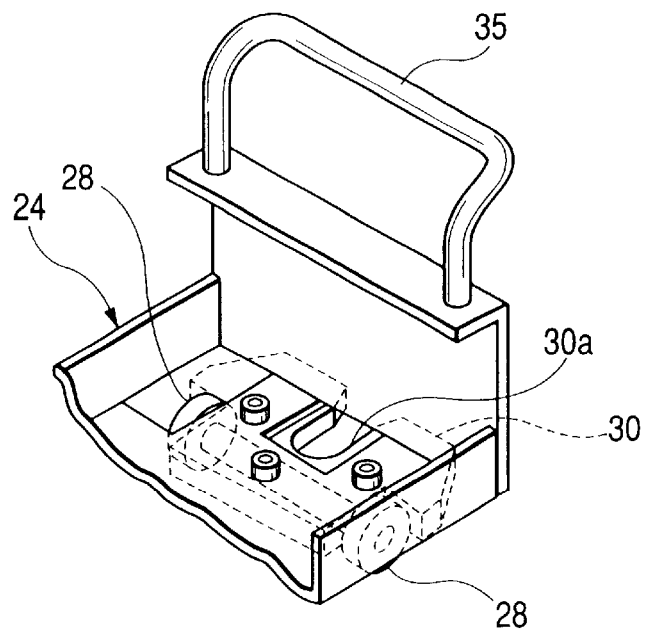
FIG. 7 is a perspective view for showing a rear portion of the tray in the same sample exchanger.
Figure 8:
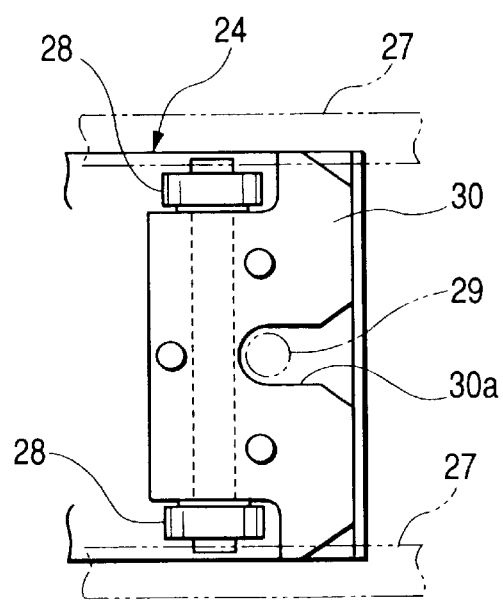
FIG. 8 is a bottom view for showing engaging members of the rear portion of the tray.

On a lower surface at the rear portion of the above-mentioned tray 24, there is provided a pair of rollers 28 at the left-hand side and the right-hand side, which move or run on the tray mounting surface 21a of the base 21, forming as a projecting portion projecting downward therefrom, as shown in FIG. 7. Those rollers 28 move along inside the guide rails 27 shown in FIG. 8, thereby guiding the pull-out and the return back of the tray 24 from and to the storage position thereof. Further, on the lower surface of the rear portion of the tray 24, there is fixed an engagement member 30 having an engagement groove 30a, into which can be engaged an engagement pin 29, being provided behind the storage position of the each tray 24 on tray mounting surface 21a of the base 21, respectively, projecting therefrom. The above-mentioned rollers 28 are pivotally supported on the lower surface of the engagement member 30.

Figure 5:
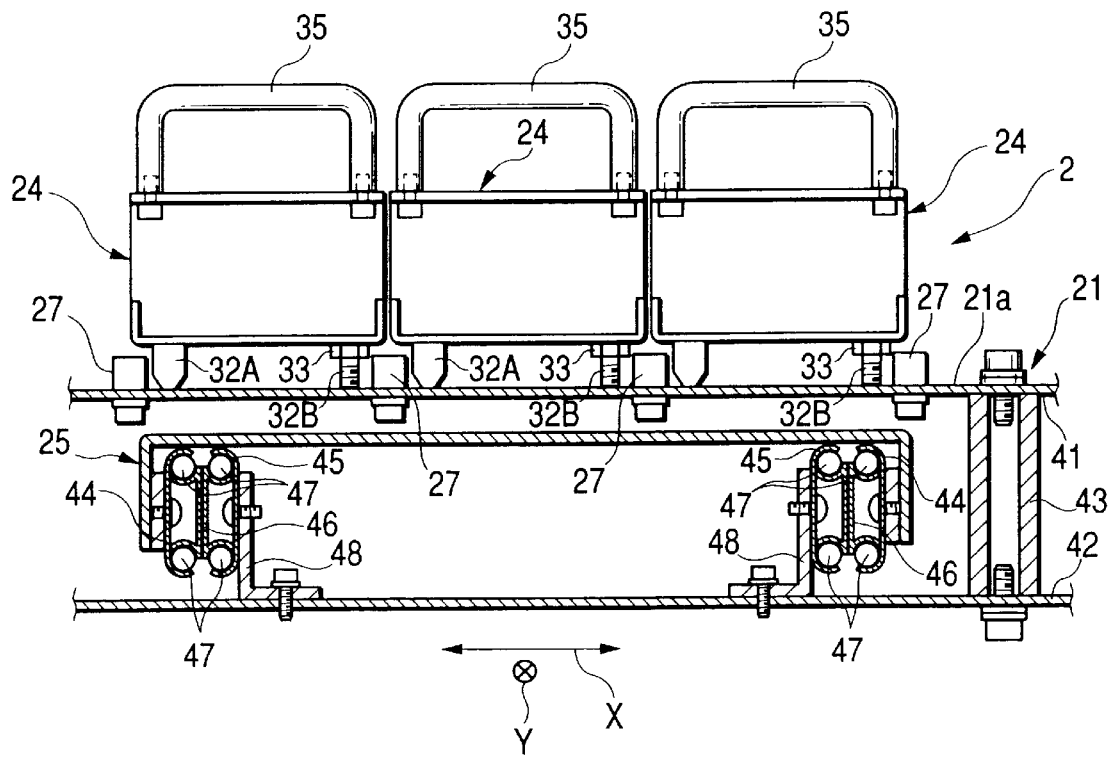
FIG. 5 is a side cross-section view seen from a front side of the same sample exchanger.

Also, on the tray mounting surface 21a of the base 21 shown in the FIG. 2, at the position corresponding to the front portion of the tray 24 when laying in the storage position, there is provided a positioning member 31 for positioning the pull-out position of the tray 24, by abutting upon the above-mentioned rollers 28 as the projecting portion on the lower surface of the rear portion of the pulled-out tray 24 when it is pulled out, extending in the horizontal direction X. Also, on the lower surface of the front portion of the above-mentioned tray 24, as shown in FIG. 5, there are provided a pair of projecting engagement portions 32A and 32B, being divided into the left-hand side and the right-hand side. Between them, the engagement portion 32B at one side thereof is made from a male screw screwing with a nut 33 which is fixed on the lower surface of the tray 24, thereby it is adjustable at a height of projection thereof, so that the tray 24 can be supported in a stable horizontal position on the tray mounting surface 21a of the base 21.

Figure 6:
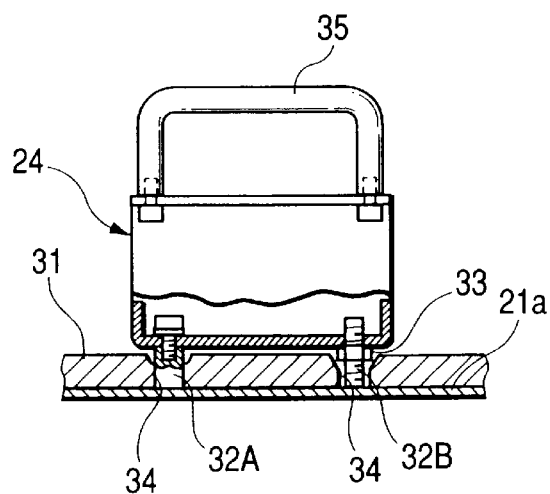
FIG. 6 is a side view, including the cross-section view of a part thereof, for showing the condition that the tray is stored within the same sample exchanger.

As is shown in the FIG. 6, in the above-mentioned positioning member 31 which is provided at the front portion of the base 21, there are provided a pair of first engaged portions 34, each being made with bores, into which the above-mentioned pair of the engagement portions 32A and 32B of the each tray 24 are engaged with, corresponding to each of the trays 24 respectively.

An upper structure, which is connected to the upper portion of legs 21b (FIG. 1) of the base 21, as shown in the FIG. 5, is constructed with an upper surface member 41 and a lower surface member 42 constructing the tray mounting surface 21a, which are connected to each other through a spacer 43. In a space defined between those upper and lower surface members 41 and 42, there are provided the jigs 25 of movement catcher mentioned above, while being able to be pulled out freely therefrom. on both side portions of this jig 25 of movement catcher are fixed the guide rails 44 extending into the pull-out direction (the vertical direction X) thereof, while on the lower surface member 42 are supported a pair of guide rails 45 at the left-hand side and the right-hand side thereof, extending in the vertical direction Y, so that they oppose to the guide rails 44, respectively from the inside thereof. Between the both guide rails 44 and 45 are positioned sliding members 46 being freely slidable in the vertical direction Y, and a plural number of balls 47 lie between the lower surfaces of the upper portions of those both guide rails 44 and 45 and the upper surfaces of the above-mentioned sliding members 46, and between the upper surfaces of the lower portions of those both guide rails 44 and 45 and the lower surfaces of the sliding members 46, respectively, thereby the jigs 25 of movement catcher can be freely pulled out with respect to the base 21.

Further, as shown in the FIG. 2, at the front portion of the above-mentioned jigs 25 of movement catcher are provided pairs of second engaged portions 49, each being made of bores and selectively engaged with the first engaged portions 34 of the positioning member 31 on the above-mentioned base 21, with respect to the pair of the engagement portions 32A and 32B of each the above-mentioned tray 24, corresponding thereto.

Next, explanation will be given on an operation of the sample exchanger 1. When exchanging the sample S held on the sample table 2, the front edge of the tray 24 on which the sample S is held is lifted up. Thereby, as shown in the FIG. 4 (A), the pair of the engagement portions 32A and 32B at the front portion of the tray 24, being engaged with the first engaged portions 34 of the positioning member 31 at the storage position thereof, slip out from the engaged portions 34, thereby being released from the engagement. Next, after bringing the pair of the engagement portions 32A and 32B at the front portion of the above-mentioned tray 24 into the engagement with the second engaged portions 49 at the front portion of the jig of movement catcher, corresponding thereto, as shown in the FIG. 4 (B), the tray 24 is pulled out in the front direction F. Accompanying with this, as shown in the FIG. 2, the tray 24 is pulled out as one body together with the jig 25 of movement catcher. As a result of this, even under the condition of being pulled out, the tray 24 is still in the condition that the tray 24 is mounted on the jig 25 of movement catcher, therefore it is possible to support the tray 24, even being pulled out from the base 21 under the condition of cantilever, with a good stability on the base 21.

In this instance, the tray 24 may be pulled out in the front direction F after engaging two or three of others with the same one of the jig 25 of movement catcher. In a case where only one or two of the trays 24 are supported on the jig 25 of movement catcher, there occurs an excessive area 25a upon the upper surface of the jig 25 of movement catcher. Accordingly, it is possible to position the sample S itself or the sample holder 22 containing the sample S therein, which is taken out from the tray 24 and is completed with the analysis thereof, or a new sample S itself or a new sample holder containing the sample S therein, provisionally, on the excessive area, or for the operator to rest her/his arms hands thereon so as to take a comfortable position, thereby making the exchange work of the sample S easy.

Under the condition of the pulling-out mentioned above, the tray(s) 24 is restricted in the position thereof, by abutting the rollers 28 as the projecting portion on the lower surface of the rear portion of the tray 24 upon the positioning member 31 of the base 21, therefore it is possible to prevent the tray 24 from coming off from the base 21. Under the condition that the tray(s) 24 can be pulled out from the base 21 in this manner, it is of course possible for the operator of the apparatus to exchange, not only the sample(s) S laying in the front portion on the sample table 2 when the tray lies in the storage position, but also the sample(s) S located in the deep or rear portion thereof, with ease while sitting on a chair. However, new samples S themselves or new sample holders 22 setting new samples S therein are positioned on the storage table 52 shown in the FIG. 1, then when exchanging the samples, the exchange of the samples is performed by mounting the other samples S or the sample holders 22 setting the other samples S therein onto the holder mounting bases 23 on the tray 24 shown in the FIG. 2 again.

Also, as shown in the FIG. 1, in the case where the computer 53 as the controlling means of the X-rays analyzer apparatus 51 is positioned in the vicinity of the storage table 52 being separated from the sample table 2, the work of exchanging is conducted by carrying the tray 24 with grasping the handles 35 (FIG. 2) onto the storage table 52. In that instance, it is possible for the operator to conduct the setting operation of ID, i.e., input of the ID data relating to the samples can be done into the computer, every time when exchanging the sample one by one on the sample storage table 52, thereby preventing from occurring errors in the inputting operation. This ID data indicates the kind of the sample and the sizes thereof, etc., and the computer 53 sets the operating condition of the X-rays analyzer apparatus 51, which is suitable to the sample, so as to conduct the analysis automatically.

When returning the tray 24, which was once pulled out, back to the original storage position thereof, under the condition that the engagement portions 32A and 32B at the front portion of the tray 24 are engaged with the second engaged portions 49 of the jig 25 of movement catcher, it is enough that the engagement portions 32A and 32B at the front portion of the tray 24 are engaged with the engaged portions 34 of the positioning member 31 after pushing the tray 24 on the tray mounting surface 21a of the base 21. Accompanying with this push-and-back operation, the jig 25 of movement catcher is also pushed back to the original position together with the tray 24, thereby performing the push-and-back operation of the tray 24 with good stability, while being kept on the jig 25 of movement catcher.

However, in this push-and-back operation, the tray 24 enters into between the pair of the guide rails 27, which are located at the left-hand side and the right-hand side corresponding thereto, while being guided at the rear portion of the tray 24 by the guides 36, therefore it is possible to perform the push-and-back operation of the tray 24 smoothly. Also in the push-and-back operation and the pulling-out operation, the rear portion of the tray 24 can run on the tray mounting surface 21a through the rollers 28, therefore it is also possible to obtain the smooth operations of the push-and-back and the pulling-out in this aspect.

Also, in this sample exchanger 1, the plurality of the holder mounting bases 23 are mounted on one of the trays 24, being aligned in a line, therefore it is possible to perform the management of the samples S by a unit of the tray.

Although the explanation was given on the case of the sample exchanger 1 of the X-rays analyzer apparatus 51, in the embodiment mentioned above, however the present invention may be applied to the sample exchangers of the other analyzer apparatuses, such as the emission spectrophotometer, the X-ray photoelectron spectrometer, etc.

As fully mentioned in the above, according to the present invention, it is possible for the operator to handle the samples easily, even if some of them are located in the deep or rear side on the sample table, though being difficult for the operator to handle it/them, without standing up, i.e., with sitting on the chair, by pulling out the tray in front from the base. Also, separating the tray from the base to be carried in front of a computer as the controller apparatus of the X-rays analyzer, it is possible to input the ID data relating to the samples into the computer, while installing or mounting the samples on the tray, therefore the setting position of the computer should not be restricted only within the vicinity of the sample table.

What is claimed is:

1. An analyzer system equipped with a sample exchanger, comprising:
    an analyzer apparatus for analyzing a sample;
    a sample table for holding a plurality of said samples thereon; and
    a transfer means for taking out the sample from the sample table into said analyzer apparatus, wherein said sample table comprises:
    a base; and
    a tray for holding the samples thereon, being supported so that it can be pulled out in a front of the base;
    wherein said sample table further comprises a means, being pulled out in front together with the tray engaged with a lower surface thereof when the tray is pulled out, for supporting the tray on the base.

2. An analyzer system as defined in the claim 1, wherein said trays are provided in a plural number thereof, and for each of the plural number of the trays is provided said means for supporting the tray.

3. An analyzer system as defined in the claim 2, wherein a positioning member for positioning the tray is provided at a position corresponding to a front portion of said tray laying within storage position in said base, so that it abuts on a projecting portion on a lower surface of a rear portion of the tray when it is pulled out, and
    an engagement portion and a first engaged portion, for engaging with each other to hold the tray in the storage position, are provided on a front portion of the tray and on the positioning member, respectively.

4. An analyzer system as defined in the claim 3, wherein the projecting portion on the lower surface of the rear portion of the tray includes a roller which runs on a tray mounting surface of the base.

5. An analyzer system as defined in the claim 1, wherein a positioning member for positioning the tray is provided at a position corresponding to a front portion of said tray laying within storage position in said base, so that it abuts on a projecting portion on a lower surface of a rear portion of the tray when it is pulled out.

6. An analyzer system as defined in the claim 5, wherein the projecting portion on the lower surface of the rear portion of the tray includes a roller which runs on a tray mounting surface of the base.

7. An analyzer system as defined in the claim 1, wherein a positioning member for positioning the tray is provided at a position corresponding to a front portion of said tray laying within storage position in said base, so that it abuts on a projecting portion on a lower surface of a rear portion of the tray when it is pulled out, and an engagement portion and a first engaged portion, for engaging with each other to hold the tray in the storage position, are provided on a front portion of the tray and on the positioning member, respectively.

8. An analyzer system as defined in the claim 7, wherein the projecting portion on the lower surface of the rear portion of the tray includes a roller which runs on a tray mounting surface of the base.

9. An analyzer system as defined in the claim 1, wherein a positioning member for positioning the tray is provided at a position corresponding to a front portion of said tray laying within storage position in said base, so that it abuts on a projecting portion on a lower surface of a rear portion of the tray when it is pulled out, and an engagement portion and a first engaged portion, for engaging with each other to hold the tray in the storage position, are provided on a front portion of the tray and on the positioning member, respectively, and in a front portion of said means for supporting the tray is provided a second engaged portion being selectively engaged with the first engagement portion of said positioning member.

10. An analyzer system as defined in the claim 9, wherein the projecting portion on the lower surface of the rear portion of the tray includes a roller which runs on a tray mounting surface of the base.

11. An analyzer system as defined in the claim 1, wherein a positioning member for positioning the tray is provided at a position corresponding to a front portion of said tray laying within storage position in said base, so that it abuts on a projecting portion on a lower surface of a rear portion of the tray when it is pulled out, and wherein, the projecting portion on the lower surface of the rear is portion of the tray includes a roller which runs on a tray mounting surface of the base.

12. An analyzer system as defined in the claim 1, wherein said analyzer apparatus comprises an X-rays spectroscopic analyzer.

13. An analyzer system as defined in the claim 1, wherein said analyzer apparatus comprises an emission spectrophotometer.

14. An analyzer system as defined in the claim 1, wherein said analyzer apparatus comprises an X-ray photoelectron spectrometer.

15. An analyzer system as defined in the claim 1, wherein said sample includes a sample holder for holding the sample to be analyzed therein.

16. An analyzer system as defined in the claim 1, wherein said tray has a longitudinal shape.

17. An analyzer system as defined in the claim 16, wherein said tray has a pair of handles to be grasped by hand at both ends in the longitudinal direction thereof.

18. An analyzer system equipped with a sample exchanger, as defined in claim 1, wherein said tray holds the samples in a longitudinal direction of said tray, said tray being slidably aligned on said base in a direction from the front to a rear of said base so that said tray is pullable outwardly in a direction of the front of said base.

19. An analyzer system equipped with a sample exchanger, comprising:

an analyzer apparatus for analyzing a sample;

a sample table for holding a plurality of said samples thereon; and a transfer means for taking out the sample from the sample table into said analyzer apparatus, wherein said sample table comprises a base, and a plurality of trays, being supported on said base in slidable manner;

wherein each of said plurality of trays hold the samples in a longitudinal direction thereof, said trays being aligned on said base in a direction from a front to a rear of said base, in slidable manner.

* * * * *